United States Patent
Kreindel

(10) Patent No.: US 9,168,096 B2
(45) Date of Patent: Oct. 27, 2015

(54) SYSTEM AND METHOD FOR TISSUE TREATMENT USING NON-SYMMETRIC RADIO-FREQUENCY ENERGY WAVEFORM

(71) Applicant: Invasix Corp., Richmond Hill (CA)

(72) Inventor: Michael Kreindel, Richmond Hill (CA)

(73) Assignee: INVASIX CORP., Richmond Hill, Ontario (CA)

(*) Notice: Subject to any disclaimer, the term of this patent is extended or adjusted under 35 U.S.C. 154(b) by 81 days.

(21) Appl. No.: 14/021,006

(22) Filed: Sep. 9, 2013

(65) Prior Publication Data

US 2015/0073401 A1  Mar. 12, 2015

(51) Int. Cl.
| | | |
|---|---|---|
| A61B 18/14 | (2006.01) | |
| A61B 18/18 | (2006.01) | |
| A61B 18/12 | (2006.01) | |
| A61B 18/00 | (2006.01) | |

(52) U.S. Cl.
CPC .............. *A61B 18/18* (2013.01); *A61B 18/12* (2013.01); *A61B 2018/00613* (2013.01)

(58) Field of Classification Search
CPC .............. A61B 18/14; A61B 18/1206; A61B 2018/0016; A61B 2018/00613
See application file for complete search history.

(56) References Cited

U.S. PATENT DOCUMENTS

| | | |
|---|---|---|
| 5,660,836 A | 8/1997 | Knowlton |
| 5,755,753 A | 5/1998 | Knowlton |
| 5,919,219 A | 7/1999 | Knowlton |
| 5,948,011 A | 9/1999 | Knowlton |
| 6,377,854 B1 | 4/2002 | Knowlton |
| 6,377,855 B1 | 4/2002 | Knowlton |
| 6,378,380 B1 | 4/2002 | Kusters et al. |
| 6,430,446 B1 | 8/2002 | Knowlton |
| 6,438,424 B1 | 8/2002 | Knowlton |
| 6,461,378 B1 | 10/2002 | Knowlton |
| 6,470,216 B1 | 10/2002 | Knowlton |
| 6,662,054 B2 | 12/2003 | Kreindel et al. |
| 6,697,670 B2 | 2/2004 | Chomenky et al. |
| 6,749,626 B1 | 6/2004 | Bhat et al. |
| 6,831,498 B2 | 12/2004 | Marsh |
| 2002/0169394 A1* | 11/2002 | Eppstein et al. ............. 600/573 |
| 2003/0149451 A1 | 8/2003 | Chomenky et al. |
| 2004/0019371 A1 | 1/2004 | Jaafar et al. |
| 2006/0015165 A1* | 1/2006 | Bertolero et al. ............ 607/119 |
| 2007/0161982 A1 | 7/2007 | Chornenky et al. |
| 2010/0023004 A1* | 1/2010 | Francischelli et al. .......... 606/41 |
| 2011/0112520 A1* | 5/2011 | Michael .......................... 606/13 |

OTHER PUBLICATIONS

Stephen J. Beebe et al; Nanosecond, high-intensity pulsed electric fields induce apoptosis in human cells; The Faseb Journal, vol. 17 dated Aug. 2003, pp. 1493-1495.
Hee K. Lee; Electrical Sterilization of Juice by Discharged HV Impulse Waveform; American Journal of Applied Sciences ; vol. 3, Issue 10; pp. 2076-2078.

* cited by examiner

*Primary Examiner* — Michael Peffley
*Assistant Examiner* — Daniel Fowler
(74) *Attorney, Agent, or Firm* — Allen Dyer Doppelt Milbrath & Gilchrist

(57) ABSTRACT

A method for soft tissue destruction comprises applying high voltage pulses causing irreversible electroporation alternating with low amplitude pulses of opposite polarity balanced to provide negligible average current and minimize risk of electrical shock. The method may be accompanied by tissue heating to reduce the electroporation threshold and negative pressure for skin shaping and optimal voltage distribution.

22 Claims, 3 Drawing Sheets

SYSTEM AND METHOD FOR TISSUE TREATMENT USING NON-SYMMETRIC RADIO-FREQUENCY ENERGY WAVEFORM

FIELD OF THE INVENTION

The invention relates to methods and devices for tissue destruction, and more particularly, to methods and devices using irreversible electroporation.

BACKGROUND OF THE INVENTION

Electrical energy is used for tissue distraction mainly in two forms. In one form, radio-frequency (RF) energy is used to create thermal tissue destruction. The advantage of high frequency alternating current is pure thermal effect. At frequencies above 100 kHz the electrical current does not affect the nerves significantly, while the high density electrical current flowing through the tissue creates Joule heat increasing tissue temperature to the necrotic level. RF energy is actively used in electro-surgery and for tissue coagulation. Electrosurgery was pioneered by Bovie (U.S. Pat. No. 1,813,902) in 1928 and since that time different design of devices were suggested and multiple clinical applications were developed. RF is associated with surgical procedures and requires anesthesia to reduced pain associated with thermal tissue destruction. Recently, RF became popular for sub-necrotic tissue heating where the heat level is not high enough to generate tissue damage but stimulates physiological process in the warmed zone. For example, RF energy has been actively used for collagen remodeling in the skin. U.S. Pat. No. 6,749,626 describes the use of RF energy for collagen formation in the dermis. U.S. Pat. Nos. 6,470,216, 6,438,424, 6,430446 and 6,461,378 disclose methods and apparatuses for thermal treatment of the collagen matrix using RF, cooling and a special electrode structure that smoothes the skin surface. U.S. Pat. Nos. 6,381,498, 6,377,855, 5,919,219, 5,948,011, 5,755,753 describe methods of collagen contraction using RF energy, and a reverse temperature gradient on the skin surface. U.S. Pat. Nos. 6,378,380, 6,377,854 and 5,660,836 describe methods of liposculpturing using RF energy and external cooling to affect the collagen inside the adipose tissue. Another method to reduce and redistribute adipose issue is skin massaging. This method is based on improving blood circulation and increasing fat metabolism. U.S. Pat. No. 6,662,054 describes a method for skin massaging in combination with non-aggressive RF heating for increasing skin and fat metabolism.

Another, non-thermal method of destruction of adipose tissue is irreversible electroporation (IEP). This method is based on changing cell membranes using high electrical field leading to the apoptotic death of cells. US Patent Application Publications 2004/0019371 and 2003/0149451 describe devices and methods comprising at least two electrodes and generating electrical pulses with voltage above an electroporation threshold. U.S. Pat. No. 6,697,670 describes device with two pairs of electrodes where the first pair is used for electroporation of adipose tissue and second pair for electro-stimulation.

U.S. Pat. No. 6,697,670 and Patent Application Publication 2007/0161982 describe use of symmetrical bipolar pulses for IEP. This method allows a reduction in the shocking effect by maintaining zero average current, but subsequent pulses having similar amplitude but opposite polarity does not allow a cumulative effect from multiple pulses to be reached.

High voltage (HV) pulses used for IEP may create arcing around the electrode and damage the skin surface. Using pulses with single polarity may create a risk of electrical shock. According to the above mentioned patents and applications, electroporation effect becomes more consistent when an amplitude of electrical pulses is higher, pulse duration is longer and more HV pulses are applied. All these changes increase risk of electrical shock and create risk of potential harm to the patient.

Reduction of pulse duration below 10 microseconds may reduce electrical shock sensation but will require higher amplitude of HV pulses to generate clinical effect. (Nanosecond, high-intensity pulsed electric fields induce apoptosis in human cells. STEPHEN J. BEEBE, PAULA M. FOX, LAURA J. REC, E. LAUREN K. WILLIS, AND KARL H. SCHOENBACH, The FASEB Journal, Vol. 17 August 2003, pp. 1493-1495).

HV electrical pulses are also used for sterilization destroying bacteria. In the article "Electrical Sterilization of Juice by Discharged HV Impulse Waveform", Hee-Kyu Lee, American Journal of Applied Sciences 2 (10): 2076-2078, 2006, it is shown that survivability of the cells is a strong function of temperature. Increase of temperature from 30° C. to 40° C. may provide the same survivability at an electric field strength two times lower. Pre-heating or pre-cooling of adipose tissue prior the electroporation treatment may reduce the treatment threshold to the level that is practical for use with less risk for the treated patient.

All the above mentioned methods may improve IEP treatment, but do not allow significantly reducing the electrical effect or significantly diminishing electrical shocking while providing efficient cell apoptotic destruction.

SUMMARY OF THE INVENTION

The present invention provides a method of tissue destruction using irreversible electroporation (IEP) where electrical pulses with amplitude above the IEP threshold are alternated with pulses of opposite polarity having amplitude that significantly below the IEP threshold. Amplitude, duration and waveform of positive and negative pulses are balanced to provide low or zero average voltage.

Average voltage and alternating frequency of alternating pulses should be high enough to minimize the electrical shocking effect. This method allows high voltage pulses providing IEP to be applied while minimize electrical shocking effect.

In other words IEP effect is achieved using RF voltage having a significantly non-symmetrical waveform where a half wave has high amplitude and short duration while the other half wave has low amplitude but longer duration. The voltage may have rectangular, sine, Gaussian or other form depending on the electrical circuit used.

This alternating voltage can be applied as a single cycle of alternating voltage, as a train of cycles or in continuous mode. Voltage waves with opposite polarities may applied immediately in sequence or with some delay between them. As used herein, this non-symmetrical waveform RF cycles structure is referred to as "NSRF," which term encompasses all possible variations of the above described electrical waveform.

In some cases a train of pulses with one polarity can be delivered but average current through the tissue should be below the electrical shock level.

Amplitude of the HV part of the wave providing IEP effect should create electrical field strength from a few hundred volts per centimeter up to a few thousands voltage per centimeter depending on type of tissue treatment and treatment conditions. The electric field strength used for IEP should be in the range of 200V/cm up to 10 kV/cm but the preferable range is from 300V/cm up to 5 kV/cm. Higher voltage increases the risk of electrical breakdown between electrodes in the air while at lower voltage the electroporation effect is not consistent.

The IEP treatment can be accompanied by thermal (heating or cooling) effect reducing the IEP threshold. Heating of the treated tissue can be provided using an external energy source or by the NSRF itself. As an external tissue heating source another source of RF, optical, microwave or ultrasound energy can be used or alternatively contact with a hot surface. A cooling effect can be achieved through contact with a pre-cooled surface or using dynamic cooling by evaporating liquid applied to the tissue. Pre-heating or pre-cooling of the tissue allows destroying cells at much lower electric field strength than associated with the electroporation threshold under normal conditions.

Optical energy in visible and/or infrared range can be used to pre-heat the treated tissue. Preferably, the near infrared part of light spectrum with light penetration depth more than 1 mm should be used to introduce at least part of the optical energy below the dermal layer. Gas discharge or incandescent lamps can be used as an incoherent light source with a filter optimizing light spectrum for better and safer heating. Laser also can be used for tissue heating. A laser diode with a wavelength in the range of 600 nm to 2000 nm provides good efficiency of heating. Optical energy can be delivered in pulsed and continuous wave (CW) mode to the tissue surface and into the tissue using optical fiber.

In another embodiment the tissue can be heated by heat transfer from a pre-heated thermostat attached to the tissue. This method is very inexpensive due to its simplicity but heat transfer to the depth of 1 cm can take a few minutes and prolong significantly the treatment time. As a further heat source pre-heated liquid can be used or a metal plate connected to the energy source with one side and attached to the tissue with the other side.

In all heating methods the desired tissue temperature should not exceed 45° C. to avoid tissue thermal damage and pain. In the case of cooling the tissue temperature should be above 0° C. Tissue temperature can be monitored using a thermistor, thermocouple, infrared thermometer or other methods to stop or reduce heating near the discomfort threshold.

To avoid electrical shocking, cycle of pulses of opposite polarity should be applied to tissue during a time period which is shorter than 100 microseconds but preferable below 10 μsec especially with the application of a train of cycles. The duration of a HV pulse should be in the range of 10 nanoseconds to 5 microseconds while a pulse of opposite polarity should be a few times longer.

A mono-polar electrode system can be used for small spots below a few square centimeters but a bi-polar electrode scheme is preferable where two or more electrodes are applied to the treated area.

Negative pressure can be used to shape skin in an optimal way and attach tissue to the electrodes. Typical vacuum level used for skin shaping is −200 to −600 mbar relative to normal atmospheric pressure. Lower pressure can be used but there is higher risk of bruising. For treatment of adipose tissue the vacuum cavity depth should be at least of 6 mm to allow the electrical field to penetrate uniformly into the fat layer.

This invention can be used for body contouring, face lifting and cellulite treatment. For body treatment, a larger cavity and higher heating power should be used, while for face treatment, a smaller hand piece and lower power are more suitable.

This non-symmetrical RF wave can be applied externally to the skin surface or invasively depending on clinical application.

Higher sensitivity of cells with a larger diameter to the HV allows selective destruction of larger cells. For example this allows selective targeting of fat cells without affecting skin, blood vessels or nerves.

This method can be used in cosmetic and medical procedures. One of the treatments which ideally suitable for above described method is fat destruction to improve body contour, cellulite treatment and circumferential reduction. This method also can be used for destruction of malignant or benign tumors, prostate treatment and other applications where tissue should be removed or its growth should be ceased.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF PREFERRED EMBODIMENTS

Figure 1:
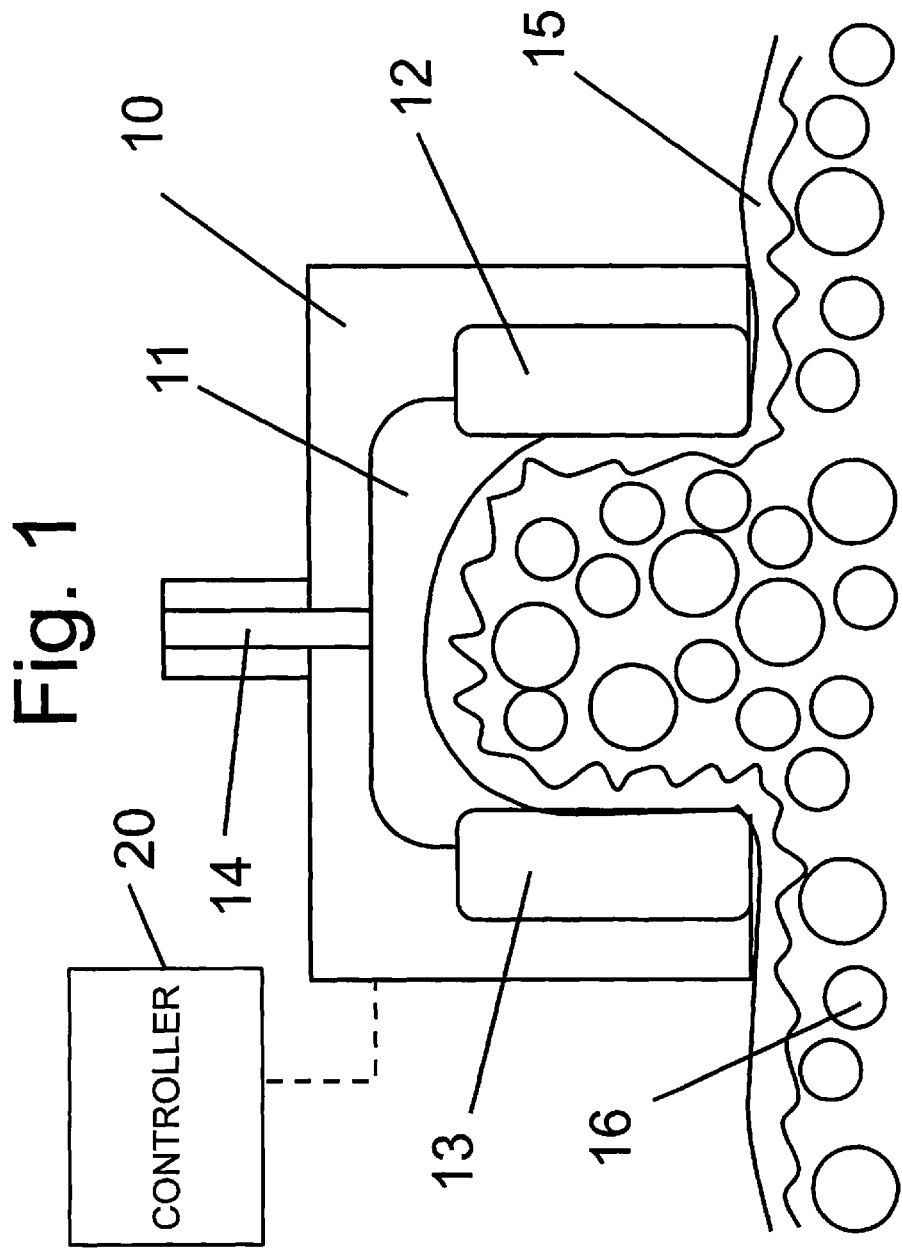
FIG. 1 shows a cavity with protruded skin and two electrodes delivering NSRF into the protruded tissue volume.

Referring first to FIG. 1, a hand piece assembly comprises a housing 10 with a cavity 11. Two RF electrodes 12, 13 are assembled inside the cavity 11. Negative pressure created through an inlet 14 pulls skin 15 and subcutaneous fat 16 into the cavity 11 and brings the skin into contact with the electrodes 12,13. This pair of electrodes 12, 13 delivers to the skin 15 and fat 16 RF energy for tissue preheating and NSRF for electroporation effect. This geometry localizes RF energy and electric field generated by HV pulses in limited volume inside the cavity reducing risk of accidental damage of other tissue.

A controller 20 is connected to the hand piece assembly and operable to supply the RF energy to the electrodes 12, 13, draw a vacuum on the inlet 14, and/or apply pre-heating or pre-cooling, as described in greater detail below.

Figure 2:
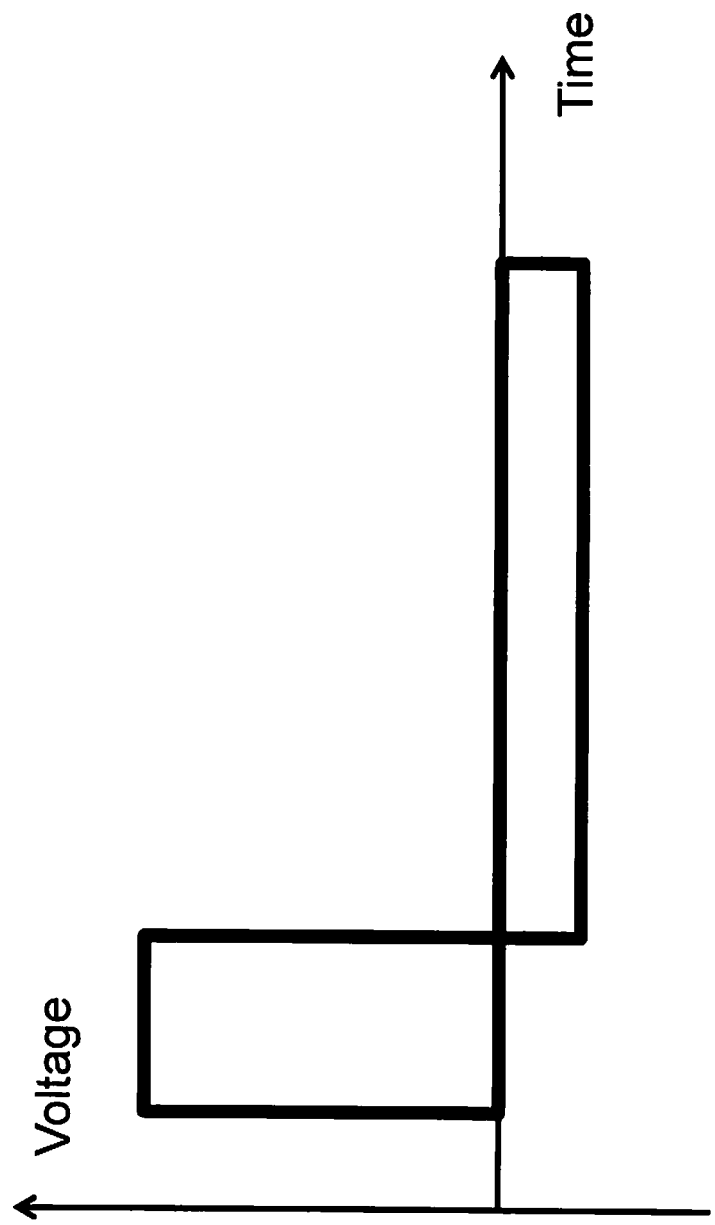
FIG. 2 shows schematic structure of one cycle of alternating voltage.

The NSRF comprises of train of non-symmetrical RF cycles as shown in FIG. 2. A wave part of a first polarity has a high amplitude and shorter duration while the other polarity wave part has a low amplitude and longer duration. The positive and negative parts of wave preferably have substantially equal areas to make average voltage close to zero and avoid electrical shock.

Figure 3:
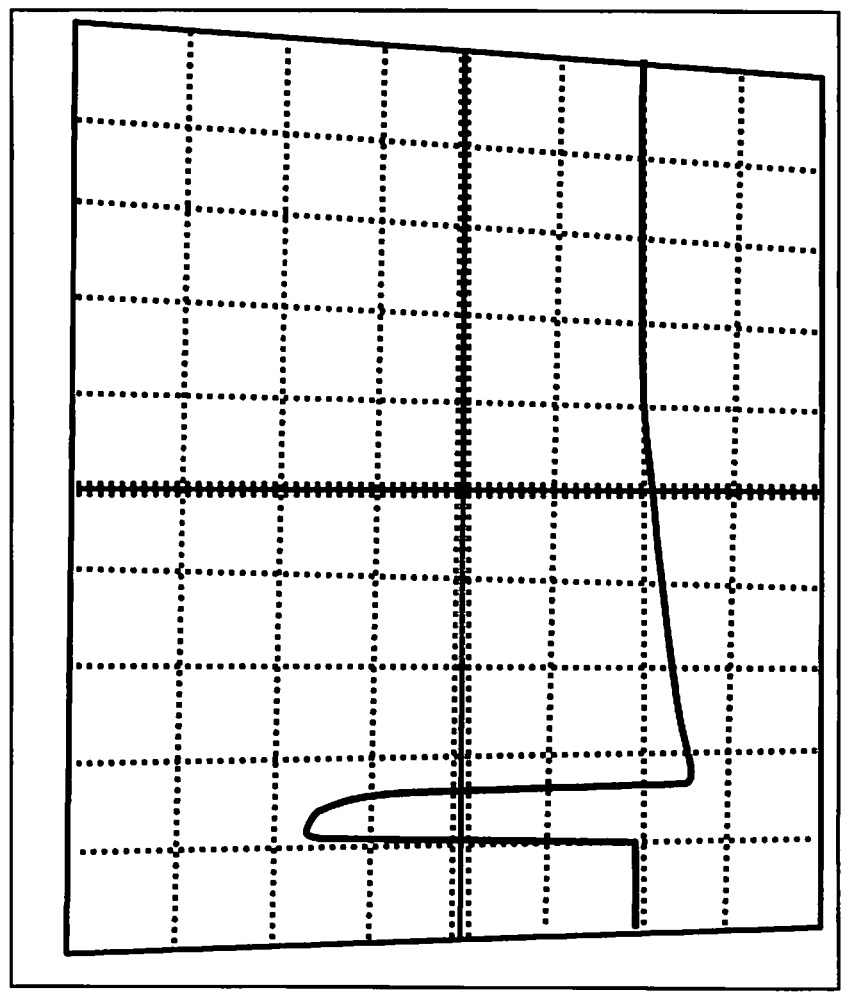
FIG. 3 shows a measured cycle non-symmetric RF cycle.

FIG. 3 shows a measured structure of the non-symmetrical RF where positive part of the wave has amplitude of 2 kV while a negative long Gaussian wave has amplitude about 300V.

In a preferred method for adipose tissue treatment using device shown in FIG. 1 the RF energy used for tissue 15 preheating and NSRF are delivered through the same RF electrodes located in the vacuum cavity 11. The treatment is conducted with following steps:

At first step the cavity 11 is applied with opening to the skin surface;

Negative pressure is applied to the cavity to aspirate part of skin with fat into the cavity and couple it to the RF electrodes 12, 13;

RF energy is applied to the tissue to increase its temperature above normal level;

When skin temperature reaches a predetermined level one or more cycles of NSRF are applied; and When negative pressure is released the hand piece is moved to a new area.

Another method comprises the following steps:

Applying one or more electrodes to the area to be treated; and

Applying one or more cycles of NSRF to the tissue via the one or more electrodes.

An alternative method comprises the following steps:

Applying one or more electrodes to the treated area;

Pre-heating or pre-cooling treated tissue to the desired temperature; and

Applying NSRF to the tissue.

The other method may include the following steps:

Shaping the skin using negative pressure;

Applying one or more electrodes to the treatment area;

Pre-heating or pre-cool treated tissue to the desired temperature; and/or

Applying NSRF to the tissue.

The other method may include the following steps:

Shaping skin using negative pressure;

Applying one or more electrodes to the treated area; and/or

Applying NSRF to the tissue.

Electrodes can be applied to the treatment area on the skin surface or inside the body.

Exemplary treatment parameters that can provide required IEP effect in all above mentioned methods are:

Amplitude of HV wave in NSRF cycle −200V-10,000V

Amplitude of low voltage wave in NSRF cycle −20V-1,000V

Vacuum level −100 mbar to −800 mbar

Tissue average pre-heating level—up to 50° C.

Tissue average pre-cooling—not lower than 0° C.

What is claimed is:

1. A method of tissue destruction using non-symmetrical radio-frequency (NSRF) irreversible electroporation (IEP), the method comprising:
   coupling at least one electrode to tissue to be treated; and
   applying at least one cycle of alternating voltage to the tissue via the at least one electrode having at least first and second wave parts having opposite polarities and unequal amplitudes;
   wherein the first wave part amplitude is above an IEP threshold and the second wave part amplitude is below the IEP threshold.

2. The method of claim 1, wherein the first and second wave parts have unequal durations.

3. The method of claim 1, wherein the average current during the at least one cycle is approximately zero.

4. The method of claim 1, wherein a train of multiple cycles with the first and second wave parts are delivered, and a pulse frequency is high enough to minimize electrical shocking.

5. The method of claim 1, wherein the first wave comes before the second wave part in the cycle.

6. The method of claim 1, further comprising applying pre-heating or pre-cooling to the tissue prior to applying the at least one cycle of alternating voltage.

7. The method of claim 6, wherein pre-heating is applied using at least one of:
   RF energy;
   optical energy; and
   contact with a heated surface.

8. The method of claim 6, wherein pre-heating is applied to achieve an average tissue temperature of up to 50 degrees C.

9. The method of claim 6, wherein pre-cooling is applied using contact with a cooled surface.

10. The method of claim 6, wherein pre-cooling is applied to achieve an average tissue temperature of down to 0 degrees C.

11. The method of claim 1, further comprising applying negative pressure to couple the at least one electrode to the tissue.

12. The method of claim 11, wherein a vacuum level of the negative pressure is between −100 mbar and −800 mbar.

13. The method of claim 1, wherein the tissue is to be treated in connection with at least one of: body weight reduction, local fat reduction, cellulite reduction, face lifting, prostrate treatment, and tumor treatment.

14. A method of tissue destruction using non-symmetrical radio-frequency (NSRF) irreversible electroporation (IEP), the method comprising:
   coupling at least one electrode to tissue to be treated; and
   applying at least one cycle of alternating voltage to the tissue via the at least one electrode having at least first and second wave parts having opposite polarities and unequal amplitudes, the first wave part amplitude being above an IEP threshold and the second wave part amplitude being below the IEP threshold, and the first wave part duration being shorter than the second wave part duration such that the average current during the at least one cycle is approximately zero.

15. The method of claim 14, wherein a train of multiple cycles with the first and second wave parts are delivered, and an average pulse frequency is high enough to minimize electrical shocking.

16. The method of claim 15, wherein the average pulse frequency is at least 10 kHz.

17. The method of claim 14, wherein the first wave part amplitude is at least 200 V.

18. The method of claim 17, wherein the first wave part amplitude is between 200 V and 10,000 V.

19. The method of claim 14, wherein the second wave part amplitude is no greater than 1,000 V.

20. The method of claim 19, wherein the second wave part amplitude is between 20 V and 1,000 V.

21. The method of claim 14, wherein the average current during the at least one cycle is below 100 mA.

22. The method of claim 21, wherein the average current during the at least one cycle is below 10 mA.

* * * * *